(12) United States Patent
Bense et al.

(10) Patent No.: US 8,674,705 B2
(45) Date of Patent: Mar. 18, 2014

(54) DEVICE FOR THE CONTACT-LESS DETECTION OF THE DEGREE OF DRYNESS OF A COAT OF VARNISH, AND METHOD FOR THE SAME

(75) Inventors: Rolf Bense, Jork (DE); Rebecca Siewert, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 444 days.

(21) Appl. No.: 13/010,319

(22) Filed: Jan. 20, 2011

(65) Prior Publication Data

US 2011/0199098 A1    Aug. 18, 2011

Related U.S. Application Data

(63) Continuation of application No. PCT/EP2009/058627, filed on Jul. 7, 2009.

(60) Provisional application No. 61/188,099, filed on Aug. 6, 2008.

(30) Foreign Application Priority Data

Aug. 6, 2008    (DE) .......................... 10 2008 041 052

(51) Int. Cl.
*G01R 27/04*    (2006.01)

(52) U.S. Cl.
USPC .......................................................... 324/637

(58) Field of Classification Search
USPC .......................................................... 324/637
See application file for complete search history.

(56) References Cited

U.S. PATENT DOCUMENTS

| 3,220,378 A |   | 11/1965 | LeFevre et al. |
| 4,485,284 A | * | 11/1984 | Pakulis .......................... 219/705 |
| 5,233,762 A | * | 8/1993  | Muller et al. ................... 34/246 |

(Continued)

FOREIGN PATENT DOCUMENTS

| DE | 197 37 785 A1 | 3/1999 |
| DE | 198 34 184 A1 | 2/2000 |

(Continued)

OTHER PUBLICATIONS

Chinese Office Action for Application Serial No. CN 2009/801305911 dated Apr. 5, 2012.

(Continued)

*Primary Examiner* — Jeff Natalini
(74) *Attorney, Agent, or Firm* — Jenkins, Wilson, Taylor & Hunt, P.A.

(57) ABSTRACT

A device and method for the contactless and therefore non-destructive measurement of a degree of dryness of a coat of paint applied to a substrate. The device comprises at least one transmitter for electromagnetic radiation, at least one receiver for determining the absorption of the electromagnetic radiation radiated into the coat of paint, and a measuring means. In the measuring means, the raw measured values measured by the receiver are processed and the degree of dryness, calculated therefrom, of the coat of paint is displayed. Either microwave radiation or infrared radiation in the near infrared range is used as measuring radiation, at least one time-dependent measurement of the absorption at a constant wavelength being made in both cases. In addition, the invention relates to a method for determining the degree of dryness of a coat of paint by means of the device.

6 Claims, 2 Drawing Sheets

(56) References Cited

U.S. PATENT DOCUMENTS

| | | | |
|---|---|---|---|
| 5,937,761 | A | 8/1999 | Buschmann et al. |
| 6,447,836 | B1 | 9/2002 | Schrof et al. |
| 7,987,717 | B2 * | 8/2011 | Casagrande et al. ............ 73/573 |
| 2005/0075463 | A1 | 4/2005 | Zarnoch |
| 2007/0199370 | A1 | 8/2007 | Diedrich et al. |

FOREIGN PATENT DOCUMENTS

| | | |
|---|---|---|
| DE | 102004053734 | 5/2006 |
| JP | 2005-045288 | 2/1993 |
| JP | 2005-172646 A | 6/2005 |
| WO | WO 03/034042 A | 4/2003 |

OTHER PUBLICATIONS

Day, David R. et al: "In-Process Endpoint Determination of Hercules 3501-6" 36th Internat'l Sampe Symposium, pp. 571-581, Apr. 15-18, 1991.

Xu, James J.: "FTIR Analysis of Polyester Enamel Cure" *Proceedings of the Electrical/Electronics Insulation Conference*, XP-00253254 1995.

German Office Action for DE 10 2008 041 052.7 dated Feb. 26, 2009.
German Office Action for DE 10 2008 041 052.7 dated Jun. 4, 2009.
International Search Report and Written Opinion for PCT/EP09/058627 dated Jan. 28, 2010.

\* cited by examiner

DEVICE FOR THE CONTACT-LESS DETECTION OF THE DEGREE OF DRYNESS OF A COAT OF VARNISH, AND METHOD FOR THE SAME

CROSS-REFERENCE TO RELATED APPLICATIONS

This application is a continuation of PCT/EP2009/058627 filed Jul. 7, 2009 and claims priority to U.S. Provisional Application No. 61/188,099, filed Aug. 6, 2008 and German Patent Application No. 10 2008 041 052.7, filed Aug. 6, 2008, the entire disclosures of which are herein incorporated by reference.

FIELD OF THE INVENTION

The invention relates to a device for the contactless determination of a degree of dryness of a coat of paint on a substrate, in particular an outer skin of an aircraft.

In order to meet increasingly varied customer requirements with regard to the design of passenger aircraft in terms of colour, a wide variety of systems must be used for painting the aircraft. The drying times of the paint depend on a plurality of parameters. For example, the type of paint used, the air temperature and the humidity in the painting hall are important factors. In addition, the chemical composition of the paint used plays a decisive role, since the curing times vary considerably depending, for example, on whether the paint is a single-component or multi-component paint, and whether it is water-soluble or solvent-based.

Currently, the respective degree of cure of a coat of paint is usually determined by manual mechanical tests. In these tests, a sharp-edged measuring member is pushed into the coat of paint. The greater the notch effect of the measuring member in the coat of paint, the less the curing of the coat of paint has progressed. The main drawback of this method of determination is that the integrity of the coat of paint is impaired. In addition, this method of determination cannot be automated and the uncertainty of the measurement is relatively high.

Drying units, in particular infrared radiators, are currently used for drying the paints in order to accelerate the production process, which drying units require a very high electrical energy input. In order to minimise the processing times of the painted aircraft and to optimise energy consumption, it is desirable to keep the operating times of the drying units as short as possible and make it possible to control them as a function of the degree of dryness of the coat of paint. This cannot be achieved with the manual measuring methods used to date.

SUMMARY OF THE INVENTION

The object of the invention is therefore to create a device which makes it possible to determine the degree of dryness of a coat of paint in an automatic and contactless manner, while achieving a high level of accuracy at the same time. A further object of the invention is to provide a method for carrying out a measurement of a degree of dryness.

This object is achieved firstly by a device having the features of claim 1.

Owing to the fact that the device comprises at least one transmitter for electromagnetic radiation, at least one receiver and a measuring means, a degree of dryness of a coat of paint can be measured with a high level of accuracy in a contactless and quantitative manner for the first time. Electromagnetic radiation of a suitable wavelength is radiated onto the surface of the coat of paint by means of the transmitter. An intensity of the electromagnetic radiation reflected (diffusely) by the surface of the coat of paint is determined by means of the receiver and passed on to a measuring unit for further evaluation, and the current degree of dryness of the coat of paint is determined therefrom.

The device can be operated using electromagnetic radiation in the range of microwave radiation with a wavelength of between 1 mm and 1 m or alternatively using electromagnetic radiation in the range of near infrared radiation (NIR) with a wavelength of between 0.8 µm and 2.5 µm.

In both cases the physico-chemical changes occurring within the coat of paint in the course of the drying process, which may for example be the outward diffusion of the respective solvent (water or chemical solvent), polymerisation processes or the like, are detected.

If microwave radiation is used, the microwaves are radiated from a suitable transmitter onto the substrate having the coat of paint. A receiver generates a measurement signal, which is prompted by the reflection. The measurement signal comprises losses as a result of the absorption in the coat of paint and in the substrate as well as further losses, for example as a result of scattering. If a distance from the transmitter and the receiver to the coat of paint and a radiation intensity of the transmitter are kept constant during the measurement of the dryness of the paint, it can be assumed that that the losses through scattering also do not change and the intensity of the microwaves received by the receiver is dependent only on the absorption within the coat of paint. The absorption at a particular wavelength is dependent on the electrical permittivity (dielectric constant) of the paint, which in turn correlates with the degree of dryness of the paint. Since there is a relationship between permittivity and drying, the respective degree of dryness can be determined by measuring the absorption. However, knowledge of the absolute intensity of the microwave radiation is not necessary, since only a change in the microwave radiation received by the receiver with respect to time, with constant output intensity and also otherwise constant environmental conditions, is evaluated by determining the first derivative of the measured curve of the microwave radiation over time.

However, if infrared radiation is used, the molecular bonds in the paint are stimulated to vibrate. Different molecular bonds require a different energy (frequency, $W=h*f$) in order to be stimulated at all. Consequently, particular molecular bonds can only be stimulated by particular frequencies in each case. As a result of the stimulation, the radiated energy is converted into kinetic energy (heat) in the paint and is thus ultimately absorbed. Consequently, particular groups of molecules absorb characteristic wavelengths in each case. Therefore, knowledge of the chemical bonds in the paint which change during the drying process is necessary for monitoring the drying characteristics of a paint by means of electromagnetic radiation in the near infrared range. One example of this is water, which evaporates during the drying process, in particular in the case of water-soluble paints. A measured curve can be determined from the measurement of the frequencies and wavelengths typically absorbed by water molecules, in which curve the reflection of these frequencies increases over time until it reaches a peak. In the case of other groups of molecules, absorption may also increase over time, for example when new groups of molecules are formed during the curing of multi-component paints. However, depending on the specific paint system used in each case, there are always frequencies at which a change in the reflection with respect to time can be measured over the relevant duration of the drying process.

On the other hand, knowledge of absolute radiation intensities is irrelevant when using infrared radiation, since the device evaluates only a gradient of the measured curve resulting from the trend of the reflection measurements with respect to time.

A development of this device provides that the measuring unit is coupled to a control and/or adjustment means.

This means that the entire measurement and evaluation sequence can be automated within the device. In addition, the combined control and/or adjustment means makes it possible to control further groups of functions within the device automatically.

According to a further advantageous configuration, it is provided that at least one drying unit, in particular at least one electric infrared radiator, is provided, which can be controlled by the control and/or adjustment means as a function of the achieved degree of dryness of the coat of paint, in particular which can be switched off automatically when an intended degree of dryness is achieved.

In this way, an automatically operating drying means can be provided downstream of a fully automated painting means.

According to a further configuration of the invention, it is provided that the electromagnetic radiation emitted by the transmitter is shortwave infrared radiation. This results in a simplified construction of the device compared to a measurement using microwaves. The near infrared radiation is radiated by the transmitter in a spectral range with a wavelength of between preferably 0.8 μm and 2.5 μm, picked up by the receiver, measured and evaluated by the measuring means in order to quantify the degree of dryness.

Further advantageous configurations of the device are set out in the further claims.

In addition, the object of the invention is achieved by a method according to claim 5, whereby the degree of dryness is determined by means of the device over the entire drying interval of up to 48 h in each case by measuring a diffuse reflection as a function of a wavelength of shortwave infrared radiation (NIR) or by measuring a diffuse reflection of microwave radiation with a particular wavelength. The time intervals between the individual absorption measurements move in a range of between 1 s and 10 minutes as a function of a memory capacity in the measuring means.

Using the method, it is possible for the first time to determine in a relatively precise, contactless and therefore non-destructive manner the degree of cure of a coat of paint applied to a substrate, thereby allowing integration into fully automated painting and drying systems for the first time.

DESCRIPTION OF EXEMPLARY EMBODIMENTS

Figure 1:
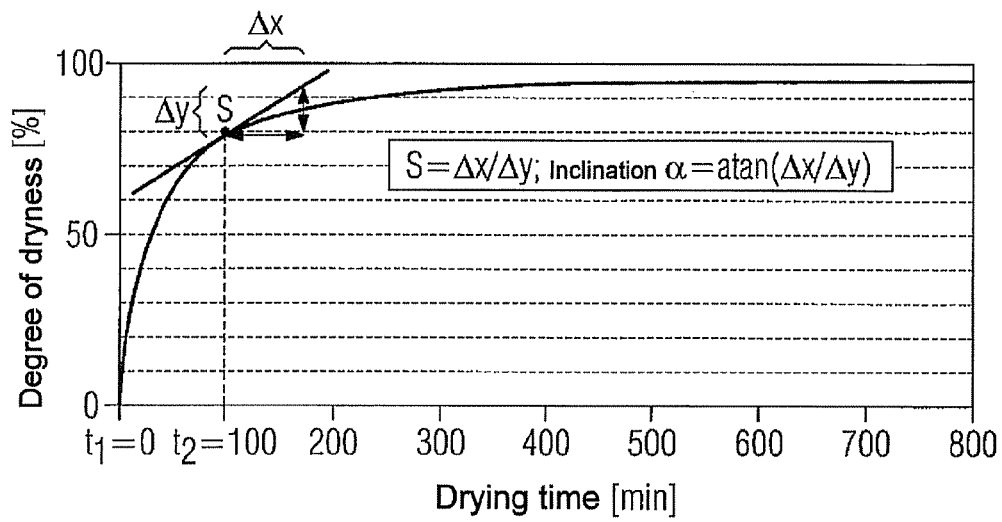
FIG. 1 is a graph showing a trend of the degree of dryness of a coat of paint as a percentage over the elapsed drying time in minutes.

The graph in FIG. 1 shows firstly the trend with respect to time of a drying process, given by way of example, of a coat of paint, as can be determined using the device according to the invention.

The degree of dryness achieved in each case is shown as a percentage on the vertical y-axis of the graph, while the previously elapsed drying time in minutes is shown on the horizontal x-axis. It is clear that at time $t_2=100$ minutes, i.e. when a gradient S, i.e. the derivative of the drying curve after time t, has reached a value of approximately 0.6 (corresponding to 35°), a degree of dryness of approximately 80 percent is already achieved. Consequently, a further prolongation of the drying duration $t_2-t_1$ is generally no longer expedient once the measured curve falls below a gradient S of 0.6 at $t_2=100$ minutes. A value of $S \leq 0.3$ is already a suitable termination criterion for the automatic control of the drying process in the case of paint systems used in aircraft construction.

Figure 2:
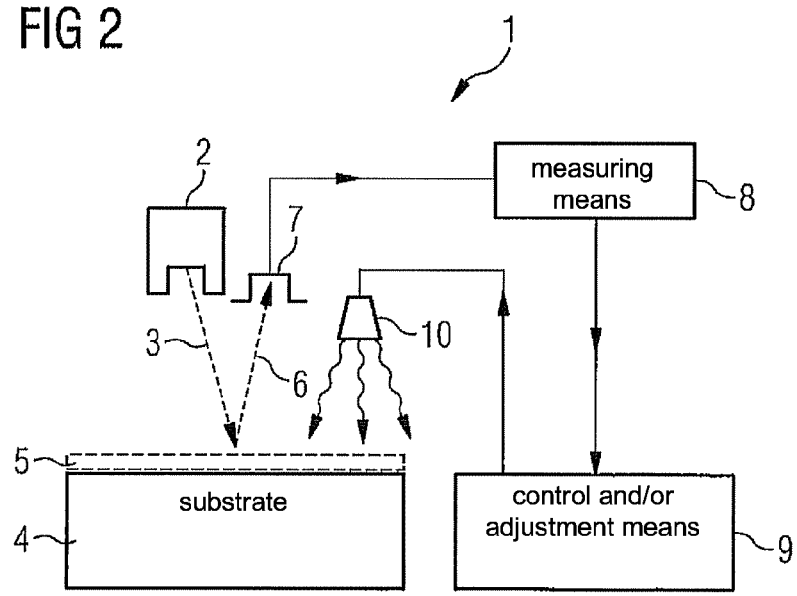
FIG. 2 shows a schematic construction of the device using electromagnetic radiation in the microwave range.

FIG. 2 shows the basic construction of device for determining the current degree of dryness or cure of a coat of paint applied to a substrate.

The device 1 comprises a transmitter 2 which in a first variant emits electromagnetic radiation in the microwave range. The transmitter 2 generally comprises drive electronics (not shown) and a radiator which is connected thereto and which is adapted to the respective wavelength of the electromagnetic radiation to be emitted.

The transmitter 2 radiates microwave radiation 3 onto a coat of paint 5 applied to a substrate 4. The microwave radiation 6 reflected from the coat of paint 5 is picked up by a receiver 7 adapted to the electromagnetic radiation used in each case, i.e. is picked up for example by an aerial in the case of microwave radiation, and is passed on to a measuring means 8 connected downstream to amplify, process (filter, etc.), digitise and numerically evaluate the raw measured values picked up by the aerial 7. In the measuring means 8, the microwave radiation 6 reflected by the coat of paint 5 and/or by the substrate 4 and received by the receiver is measured. Preferably, the raw measured values are already processed mathematically in the measuring means 8. The measured values which are amplified, processed and evaluated in the measuring means 8 can directly be displayed by an output means and/or passed on to a control and adjustment means 9, for example in order to switch off a drying means automatically when a preselected degree of dryness is achieved. For example, the trend of the absorption with respect to time $A(\lambda,t)$ at a particular wavelength or frequency ($\lambda * f = c$) can be shown graphically on a suitable indicator, display, monitor, screen or the like. A suitable drying means is preferably composed of a plurality of electrically operated infrared radiators 10 arranged in the form of a matrix, in order to control the temperature of the coat of paint 5 over a large surface area and as uniformly as possible, so as to accelerate the drying process. The measuring means 8 and the control and adjustment means 9 can be components of an integrated computer unit, in particular a conventional personal computer (for example, a PC).

The microwave radiation 3 emitted by the transmitter 2 is absorbed in the coat of paint 5 and/or by the substrate 4 as a function of the current permittivity, which in turn depends on the degree of cure of the coat of paint 5. The proportion of the microwave radiation 6 which is reflected or not absorbed by the coat of paint 5 or the substrate 4 is subsequently measured by the receiver 7. The radiator of the transmitter 2 for microwaves and the aerial, as a receiver 7, can be configured as an integral component. In the measuring means 8, an absorption A(t) is determined from the difference between the intensity, which is generally known, of the microwave radiation 3 emitted by the transmitter 2 and the intensity, which can be determined by the receiver 7, of the reflected microwave radiation 6, and this absorption correlates to a large extent with the trend of the degree of dryness of the coat of paint 5. The control and/or adjustment means 9 can then, for example, switch off a drying means formed from one or more infrared radiators 10 when, at a drying time $t_1$ in question, i.e. 100 minutes after the start $t_0$ of the drying process for example, the gradient S of the measured curve (see FIG. 1) is for example less than or equal to 0.3, since in this case a significantly higher degree of dryness can no longer be achieved even by disproportionately prolonging the curing time. The gradient S corresponds to the inclination of a tangent applied to the measured curve at the drying time $t_1$ in question. In addition, the wavelength of the microwave radiation can also be varied, in order to determine a wavelength- and time-dependent trend of the absorption $A(\lambda,t)$.

In an alternative variant (not shown in the drawings), the device 1 is operated using electromagnetic radiation in the "near infrared range" or "near infrared spectrum" between 0.8 μm and 2.5 μm ("NIR radiation"). In this case the diffuse reflection measuring method is used as a measuring method. In this variant, the transmitter 2 can for example be composed of one or more semiconductor IR diodes which radiate electromagnetic radiation with a constant wavelength in the near infrared range onto the coat of paint 5. The receiver 7 comprises for example at least one photodiode for evaluating the infrared radiation reflected by the coat of paint 5 or the substrate, the diffuse IR radiation received by the receiver being converted into an electrical output signal, i.e. being processed accordingly in the measuring means 8, i.e. in particular being filtered, amplified, digitised and numerically processed by a derivative with respect to time. The change in the absorption with respect to time $A(\lambda,t)$, which is of interest here, can be determined from the measurement signal generated by the receiver 7 at the respective wavelength tested. Precise knowledge of the intensity of the electromagnetic radiation in the wavelength or frequency range of near infrared emitted by the transmitter 2 is not necessary, since the drying of the paint can generally be regarded as ending at a gradient S≤0.3 of the measured curve (see FIG. 1), for example. In this context, an absolute measurement is therefore not important.

The near infrared radiation or IR radiation emitted by the transmitter 2 is in an energy range of the vibration level of the molecules contained in the coat of paint 5, i.e. the absorption of the IR radiation correspondingly stimulates the intermolecular bonds to vibrate. These conditions of vibration are visible in the measured absorption spectrum $A(\lambda,t)$ in the form of peaks and troughs, as shown in the graph in FIG. 3 by way of example. Since the associated energies or frequencies of the radiation are characteristic of the prevalent bonds in each case, specific chemical compositions or molecules can be identified. Since the constitution or composition of the coat of paint 5 varies continuously as a result of the drying process owing to the complex chemico-physical processes taking place, and these variations in the composition and the ingredients are reflected in a change in the measured IR absorption spectrum, the respective current degree of cure or drying progress of the coat of paint 5 on the substrate 4 can be derived therefrom.

Figure 3:
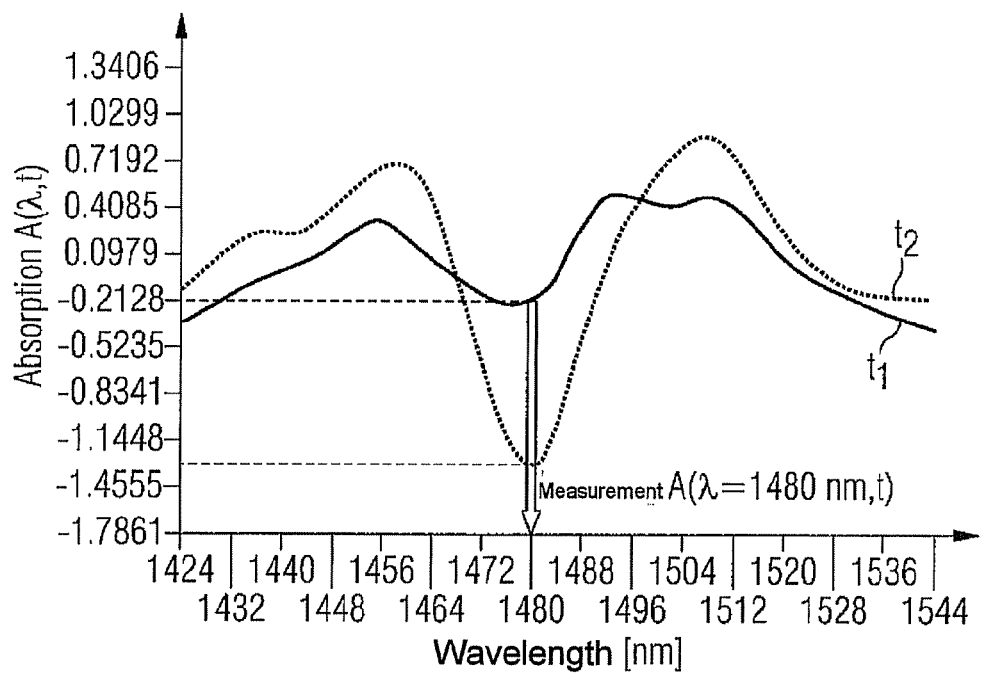
FIG. 3 shows a measured curve determined using the device in the case of electromagnetic radiation in the near infrared range (NIR)
Figure 4:
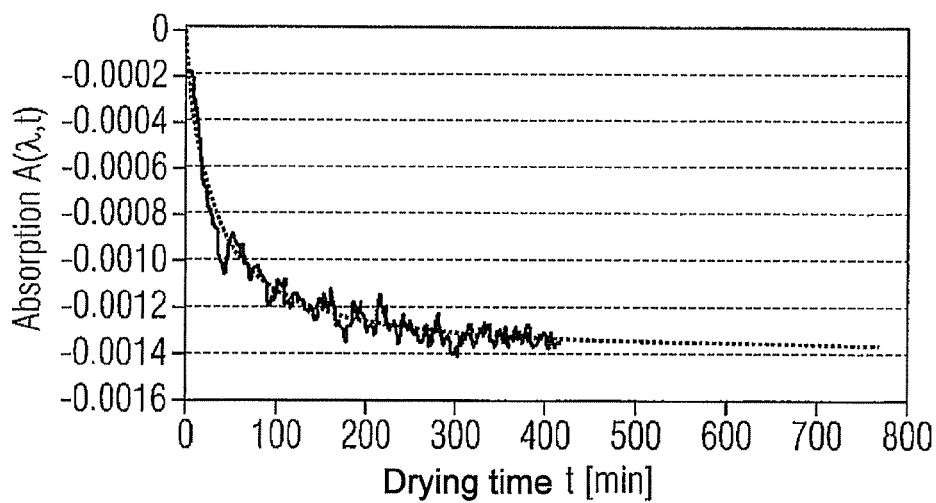
FIG. 4 shows a trend, determined from the measured curve according to FIG. 3, of the absorption with respect to time $A(\lambda,t)$ using a wavelength of $\lambda=1480$ nm, and an approximate curve calculated numerically for this purpose.

The measured curves for the absorption $A(\lambda,t)$ displayed in FIGS. 3,4 reflect merely the qualitative trend thereof and are not intended for determining quantitative absorption values.

Measuring the trend of the absorption $A(\lambda,t)$ at a wavelength of the IR radiation of approximately $\lambda$=1480 nm, for example, has proven advantageous for determining the degree of dryness of paints or paint systems currently used in aircraft construction, as the measured curve in FIG. 3, determined using the above-described device 1, shows. The wavelength of $\lambda$=1480 nm is typical in particular for the urethane groups (—CO—NH—R) contained in the coat of paint and is also not superimposed by any interfering absorption of the starting material in the coat of paint 5 and/or of the solvent or the thinning agent. The measured curve shows clearly that, from a start time of the drying process $t_1$ at 0 minutes up to the end time $t_2$ of the drying process at for example 800 minutes, the absorption value $A(\lambda,t)$ falls steeply until it reaches a minimum value. In the case of other paint systems, the change in the absorption with respect to time $A(\lambda,t)$, which is relevant to the evaluation, generally occurs at other wavelengths owing to a different chemical composition. In the case of water-based paint systems, for example, the absorption wavelength of water or water vapour is decisive.

Consequently, the trend of the absorption value A(80 ,t) at $\lambda$=1.48 μm correlates very well with the progress of the drying process in the coat of paint 5 on the substrate, in such a way that the absorption values $A(\lambda$=1480 nm,t) determined at this wavelength—after optionally required numerical intermediate operations in the measuring means 8—can be advantageously drawn on as a measure of the current degree of dryness of the coat of paint 5 in each case.

The measured curve drawn with a solid line in FIG. 4 shows the absorption $A(\lambda,t)$ measured using the device 1 over the entire drying period t of the coat of paint 5 between, for example, $t_1$=0 minutes and $t_2$=800 minutes at a fixed infrared wavelength of 1480 nm $A(\lambda$=1480 nm,t). The dotted line represents a numerical approximate curve, obtained by means of known mathematical methods, for the measured curve of the measured absorption $A(\lambda,t)$. As can be seen, this approximate curve is the inverse of the curve according to FIG. 1, from which the degree of dryness of the coat of paint 5 can be read directly as a percentage over the drying time t in minutes. In this way, the approximate curve according to FIG. 4, from which the drying curve according to FIG. 1 is directly derivable, can be determined by means of inversion from the raw measured curve according to FIG. 4.

The values which can be taken from the drying curve according to FIG. 1 can if necessary be used directly for display purposes by a user of the device 1. However, tracking the gradient S of the measured curve according to FIG. 1, i.e. merely the change in the absorption with respect to time $A(\lambda,t)$ in the near infrared range at a specific wavelength, is sufficient to control an active drying means comprising infrared radiators 10 in such a way that, for example, the infrared radiators 10 can be switched off by means of the control and adjustment means 9 at gradient values S≤0.3.

Further embodiments are set out below.

Embodiment 1: device for the contactless determination of a degree of dryness of a coat of paint on a substrate, in particular an outer skin of an aircraft, wherein the device comprises at least one transmitter for electromagnetic radiation, at least one receiver and a measuring means.

Embodiment 2: device according to embodiment 1, wherein the measuring means is coupled to a control and/or adjustment means.

Embodiment 3: device according to either embodiment 1 or embodiment 2, wherein at least one drying means, in particular comprising at least one electric infrared radiator, is provided, which can be controlled by the control and/or adjustment means as a function of the achieved degree of dryness of the coat of paint, in particular which can be switched off automatically when a preselected degree of dryness is achieved.

Embodiment 4: device according to any one of embodiments 1 to 3, wherein the electromagnetic radiation emitted by the at least one transmitter is shortwave infrared radiation in the near infrared range, in particular with a wavelength of between 0.8 μm and 2.5 μm.

Embodiment 5: device according to embodiment 4, wherein the degree of dryness of the coat of paint can be measured by determining a time-dependent absorption at least one constant wavelength of the infrared radiation.

Embodiment 6: device according to either embodiment 4 or embodiment 5, wherein a wavelength of the infrared radiation emitted by the transmitter can be varied, in order to measure a wavelength- and time-dependent absorption.

Embodiment 7: device according to any one of embodiments 1 to 3, wherein the electromagnetic radiation emitted by the at least one transmitter is microwave radiation, in particular in a wavelength range of between 1 mm and 1 m.

Embodiment 8: device according to embodiment 7, wherein the degree of dryness can be measured by determining a time-dependent absorption of the microwave radiation at at least one constant wavelength of the microwave radiation.

Embodiment 9: device according to either embodiment 7 or embodiment 8, wherein a wavelength of the microwave radiation emitted by the transmitter can be varied, in order to measure a wavelength- and time-dependent absorption.

Embodiment 10: method for determining a degree of dryness of a coat of paint on a substrate, in particular in accordance with a device according to any one of embodiments 1 to 6, wherein the degree of dryness of the coat of paint is determined by determining a time-dependent absorption of infrared radiation in the near infrared range, in particular at at least one constant wavelength of between 0.8 μm and 2.5 μm.

Embodiment 11: method according to embodiment 10, wherein the absorption is evaluated over a time interval, in particular over a time period of up to 48 h.

Embodiment 12: method for determining a degree of dryness of a coat of paint on a substrate, in particular in accordance with a device according to any one of embodiments 7 to 9, wherein the degree of dryness of the coat of paint is determined by determining a time-dependent absorption of microwave radiation, in particular at least one constant wavelength of between 1 mm and 1 m.

Embodiment 13: method according to embodiment 12, wherein the absorption is evaluated over a time interval, in particular over a drying period of up to 48 h.

LIST OF REFERENCE NUMERALS 1 device
2 transmitter (NIR/microwave)
3 microwave radiation (radiated)
4 substrate (for example, fuselage cell skin)
5 coat of paint
6 microwave radiation (reflected)
7 receiver
8 measuring means
9 control and/or adjustment means
10 infrared radiator

The invention claimed is:

1. A device for the contactless determination of a degree of dryness of a coat of paint on a substrate, being an outer shell of an aircraft, wherein the device comprises:
at least one transmitter adapted to emit electromagnetic radiation;
at least one receiver; and
a measuring means;
wherein the electromagnetic radiation emitted by the at least one transmitter is microwave radiation, wherein the transmitter is adapted to radiate microwave radiation onto the coat of paint applied to the substrate, the receiver is adapted to pick up the microwave radiation reflected from the coat of paint, to convert the microwave radiation into an electrical output signal, and to pass the electrical output signal to the measuring means, wherein the measuring means is adapted to determine the degree of dryness of the coat of paint by determining a time-dependent absorption of the microwave radiation at at least one constant wavelength of the microwave radiation based on the electrical output signal to determine a gradient of a measured curve resulting from the change in the absorption with respect to time based on the electrical output signal.

2. The device according to claim 1, wherein the measuring means is coupled to a control and/or adjustment means.

3. The device according to claim 1, wherein at least one drying means is provided, which is controlled by the control and/or adjustment means as a function of the achieved degree of dryness of the coat of paint, which is switched off automatically when a preselected degree of dryness is achieved.

4. The device according to claim 1, wherein the microwave radiation has a wavelength range of between 1 mm and 1 m.

5. A method for determining a degree of dryness of a coat of paint on a substrate, comprising at least one transmitter for emitting electromagnetic radiation, at least one receiver for receiving electromagnetic radiation, and a measuring means for measuring electromagnetic radiation, wherein the electromagnetic radiation emitted by the at least one transmitter is microwave radiation, wherein the transmitter radiates microwave radiation onto the coat of paint applied to the substrate, the receiver picks up the microwave radiation reflected from the coat of paint, converts the microwave radiation into an electrical output signal, and passes the electrical output signal to the measuring means, wherein the measuring means determines the degree of dryness of the coat of paint by determining a time-dependent absorption of the microwave radiation, at at least one constant wavelength of between 1 mm and 1 m based on the electrical output signal to determine a gradient of a measured curve resulting from the change in the absorption with respect to time based on the electrical output signal.

6. The method according to claim 5, wherein the absorption is evaluated over a time period of up to 48 h.

* * * * *